(12) United States Patent
Taylor et al.

(10) Patent No.: US 11,166,828 B2
(45) Date of Patent: *Nov. 9, 2021

(54) TRIAL ACETABULAR CUP AND KIT

(71) Applicant: Finsbury (Development) Limited, Leatherhead (GB)

(72) Inventors: Andrew Clive Taylor, Fishbourne (GB); Jonathan Robert Thomas Jeffers, London (GB)

(73) Assignee: Finsbury (Development) Limited, Leatherhead (GB)

( * ) Notice: Subject to any disclaimer, the term of this patent is extended or adjusted under 35 U.S.C. 154(b) by 383 days.

This patent is subject to a terminal disclaimer.

(21) Appl. No.: 15/921,440

(22) Filed: Mar. 14, 2018

(65) Prior Publication Data
US 2018/0200074 A1 Jul. 19, 2018

Related U.S. Application Data

(63) Continuation of application No. 14/856,336, filed on Sep. 16, 2015, now Pat. No. 9,949,845, which is a continuation of application No. 12/062,300, filed on Apr. 3, 2008, now Pat. No. 9,161,844.

(30) Foreign Application Priority Data

Apr. 3, 2007 (GB) .................................... 0706481
Jun. 26, 2007 (GB) .................................... 0712369

(51) Int. Cl.
A61F 2/34 (2006.01)
A61F 2/46 (2006.01)

(52) U.S. Cl.
CPC .............. *A61F 2/4609* (2013.01); *A61F 2/34* (2013.01); *A61F 2/4657* (2013.01); *A61F 2/4684* (2013.01); *A61F 2/4603* (2013.01); *A61F 2002/4668* (2013.01); *A61F 2002/4687* (2013.01); *A61F 2002/4696* (2013.01)

(58) Field of Classification Search
CPC ............ A61F 2250/0096; A61F 2/4684; A61F 2/4609; A61F 2/34; A61F 2/4657; A61F 2240/007; A61F 2002/3008; A61B 2090/3958

See application file for complete search history.

(56) References Cited

U.S. PATENT DOCUMENTS

| 5,636,255 A | 6/1997 | Ellis |
| 5,658,347 A | 9/1997 | Sarkisian et al. |
| 6,214,014 B1 | 4/2001 | McGann |
| 6,743,235 B2 | 6/2004 | Subba Rao |
| 9,949,845 B2 * | 4/2018 | Taylor ................... A61F 2/4609 |

(Continued)

FOREIGN PATENT DOCUMENTS

| EP | 1402857 A2 | 3/2004 |
| EP | 1634552 A2 | 3/2006 |

(Continued)

OTHER PUBLICATIONS https://www.ahdictionary.com/2020.*

(Continued)

*Primary Examiner* — Brian E Pellegrino
(74) *Attorney, Agent, or Firm* — Stinson LLP

(57) ABSTRACT

A trial acetabular cup having a signal generating device located thereon.

4 Claims, 11 Drawing Sheets

(56) References Cited

U.S. PATENT DOCUMENTS

| | | | |
|---|---|---|---|
| 2003/0069591 A1 | 4/2003 | Carson et al. |
| 2003/0212459 A1 | 11/2003 | Gibbs |
| 2004/0143340 A1 | 7/2004 | Tuma et al. |
| 2004/0167654 A1 | 8/2004 | Grimm et al. |
| 2004/0243148 A1 | 12/2004 | Wasielewski |
| 2005/0203536 A1 | 9/2005 | Laffargue et al. |

FOREIGN PATENT DOCUMENTS

| | | |
|---|---|---|
| EP | 1721586 A1 | 11/2006 |
| GB | 2323036 A | 9/1998 |
| WO | 2006089069 A2 | 8/2006 |
| WO | 2006109022 A2 | 10/2006 |

OTHER PUBLICATIONS

Asayama, Y., et al, "Intraoperative Pelvic Motion in Total Hip Arthroplasty", The Journal of Arthroplasty, 2004: vol. 19, No. 8, pp. 992-997.

Brodner, W., et al, "Cup Inclination and Serum Concentration of Cobalt and Chromium After Metal-on-Metal Total Hip Arthroplasty", The Journal of Arthroplasty, 2004: vol. 19, No. 8 Suppl. 3, pp. 66-70.

Echeverri S., et al, "Reliable Acetabular Cup Orientation With a New Gravity-Assisted Guidance System", The Journal of Arthroplasty, 2006: vol. 21, No. 3, pp. 413-419.

Hassan, D.M., et al, "Accuracy of Intraoperative Assessment of Acetabular Prosthesis Placement", The Journal of Arthroplasty, 1998: vol. 13, No. 1, pp. 80-84.

Kennedy, J.G., et al, "Effect of Acetabular Component Orientation on Recurrent Dislocation, Pelvic Osteolysis, Polyethylene Wear, and Component Migration", The Journal of Arthroplasty, 1998: vol. 13, No. 5, pp. 530-534.

Morlock, M.M., et al, "In Vivo Wear of Metal-on-Metal Hip Resurfacing Implants Depends Strongly on Cup Alignment", 53rd Annual Meeting of the Orthopaedic Research Society, 2007: Poster No. 1663.

Schmalzreid, T.P., et al, "The Relationship between the Design, Position, and Articular Wear of Acetabular Components Inserted without Cement and the Development of Pelvic Osteolysis", The Journal of Bone and Joint Surgery (American), 1994: vol. 76-A, No. 5, pp. 677-688.

Udomkiat, P., et al, "Cementless Hemispheric Porous-Coated Sockets Implanted with Press-Fit Technique without Screws: Average Ten-Year Follow-Up", The Journal of Bone and Joint Surgery (American), 2002: vol. 84-A, No. 7, pp. 1195-1200.

European Search Report for Application No. 08154040.3, dated Jul. 7, 2008, 6 pages.

* cited by examiner

TRIAL ACETABULAR CUP AND KIT

FIELD OF THE INVENTION

The present invention relates to an apparatus and system for use in hip joint replacement surgery. More particularly, the present invention relates to an apparatus and system which enables the correct positioning of an acetabular cup prosthesis to be achieved.

BACKGROUND OF THE INVENTION

The efficient functioning of the hip joints is extremely important to the well being and mobility of the human body. Each hip joint is comprised by the upper portion of the femur which terminates in an offset bony neck surmounted by a ball-headed portion which rotates within a socket, known as the acetabulum, in the pelvis. Diseases such as rheumatoid- and osteo-arthritis can cause erosion of the cartilage lining of the acetabulum so that the ball of the femur and the hip bone rub together causing pain and further erosion. Bone erosion may cause the bones themselves to attempt to compensate for the erosion which may result in the bone becoming reshaped. This misshapen joint may cause pain and may eventually cease to function altogether.

Operations to replace the hip joint with an artificial implant are well-known and widely practised. Generally, the hip prosthesis will be formed of two components, namely: an acetabular cup component which lines the acetabulum; and a femoral, or stem, component which replaces the femoral head. During the surgical procedure for implanting the hip prosthesis the cartilage is removed from the acetabulum using a reamer such that it will fit the outer surface of the acetabular cup prosthesis. The acetabular cup prosthesis can then be inserted into place. In some arrangements, the acetabular cup component may be held in place by a tight fit with the bone. However, in other arrangements, additional fixing means such as screws or bone cement may be used. The use of additional fixing means help to provide stability in the early stages after the prosthesis has been inserted. In some prosthesis, the acetabular cup component may be coated on its external surface with a bone growth promoting substance which will assist the bone to grow and thereby assist the holding of the acetabular component in place.

The bone femoral head will be removed and the femur hollowed using reamers and rasps to accept the prosthesis. The stem portion will then be inserted into the femur. In some cases, a femoral component of this kind may be replaced with components for use in femoral head resurfacing or for use in thrust plate technology.

The correct positioning of the acetabular cup prosthesis is crucial to the efficient and long-term operation of the replacement hip joint. Just as the natural hip wears with time, the prosthesis will also wear with time. However, if the acetabular cup prosthesis is not correctly seated in the acetabulum, the wear rate of the prosthetic implant will be significantly higher than when the cup prosthesis is in the optimal position. Without wishing to be bound by any theory, it is believed that the optimum position is in the region of about 45° across the pelvis. It is believed that current techniques result in the cup being inserted at an error of about ±20°. It is further believed that at angles of about 50° or higher, excessive wear of the prosthesis will occur. It should also be noted that it is necessary for the correct working of the prosthesis that it is correctly aligned in both anteversion and vertical tilt.

In *J. Bone Joint Surg. Am.* 76: 677-688, 1994 "The Relationship Between the Design, Position, and Articular Wear of Acetabular Components Inserted Without Cement and the Development of Pelvic Osteolytes" Schmalzreid et al reported on a radiographic follow-up study of a series of 113 cementless metal on polyethylene resurfaced hips that had been implanted between 1983 and 1997. At a mean of 5.3 years after surgery, no acetabular component was radiographically loose, but osteolysis in the pelvis was noted in 17% of hips. Of these hips, there was a significant relationship between cup angles greater than 50° and osteolysis of the ilium. A trend was also noted in the hips for increasing wear with increasing cup angle. The authors of the report proposed that a decreased contact area generates higher stresses in the polyethylene component and that these stresses are responsible for the increased wear.

A retrospective review of 75 hip arthroplasties was discussed by Kennedy et al in *J. Arthroplasty* 13, No. 5, 530-534, 1998, "Effect of Acetabular Component Orientation on Recurrent Dislocation, Pelvic Osteolysis, Polyethylene Wear, and Component Migration". This review investigated the effect of acetabular cup position on the wear of acetabular component in metal-on-polymer total hip replacements. The cementless acetabular component investigated had four anti-rotation ridges that the recommended surgical technique for the component specified that all four ridges should be in contact with the acetabular bone. In the first 38 patients, the cup was inserted in accordance with the recommended surgical technique with a mean angle of 61.9° in the frontal plane (i.e. 55° to 69°. In the subsequent 37 patients, the cups were inserted in a more horizontal position, with a mean angle of 49.7° (42° to 54°). The horizontal positioning required leaving one of the anti-rotation ridges on the acetabular component out of contact with the acetabular bone, i.e. an overhang of a few millimetres. Increased pelvic osteolysis, asymmetric wear and migration were found for the first group of patients. The increased wear, and subsequent migration and osteolysis, was attributed to the increased load per unit area, i.e. a smaller contact patch, generated by the vertically orientated cup, i.e. rim loading.

In *J Bone Joint Surg Am* 84-A, 1195-1200 "Cementless Hemispherical Porous-Coated Sockets Implanted with Press-fit Technique Without Screws; Average Ten-year Follow-up" Udomkiat P et al performed a 10-year follow up study of the Anatomic Porous Replacement cementless acetabular cup from Sulzer which had been used in metal-on-polymer low friction total hip replacements. This study considered 110 patients with replacements performed between 1988 and 1990. Volumetric and linear wear rates were significantly associated with younger patients and increased cup angle, i.e. more vertical orientation. No explanation is provided for the relationship between increased cup angle and increased wear, but the authors do mention that they now strive to keep abduction angles of the cup at ≤40°.

Brodner W et al, in "Cup Inclination and Serum Concentration of Cobalt and Chromium After Metal-on-Metal Total Hip Arthroplasty" *J. Arthroplasty* 19, 66-70, 2004, investigated whether cup inclination had an influence on the wear rate of metal-on-metal small diameter total hip replacements by measuring cobalt and chromium serum levels. Out of 330 patients, three groups of 20 were selected, based on their cup inclination angle. There was no significant difference between the cobalt levels ($\rho$=0.23) or the chromium levels ($\rho$=0.13) for the three groups, however three patients in the largest inclination angle group had notably higher metal ion levels. The authors concluded that metal cups with large inclination angles might be at risk of increased metal release.

Reduced load transfer area was identified as the likely reason for increased wear with larger inclination angles.

A retrieval study "In Vivo Wear of Metal-on-Metal Hip Resurfacing Implants Depends Strongly on Cup Alignment" by Mortlock et al in 53rd Proceedings Orthopaedic Research Society Poster 1163, 2007 attempted to find a relationship between excessive wear and acetabular cup angle of 14 retrieved resurfacings. The results showed that there was a strong relationship between rim loaded implants, which were identified by wear patches extending to the edge of the cup, and high rates of wear. Cup inclination tended to be about 14° higher for the rim loaded implants, but cup inclination alone was not thought sufficient to define rim loading.

It will therefore be understood that correct acetabular cup orientation is therefore essential in total hip replacement/hip resurfacing. Various so-called "aerial" alignment guides have been suggested to assist the surgeon to correctly seat the acetabular cup prosthesis. These alignment guides are crude measuring devices that are subject to error depending on the position of the patient on the table.

The failure of these aerial guides to provide reliable positioning of the acetabular cup prosthesis was highlighted by Hassan et al in *J. Arthroplasty* 13, 80-84, 1998 "Accuracy of Intraoperative Assessment of Acetabular Prosthesis Placement". In the described study four experienced surgeons performed a series of 50 total hip replacements. Using a conventional aerial guide, their goal was to position the cup between 30° and 50° vertical tilt and between 5° and 25° anteversion. Intraoperative assessment identified 47 of 50 cups being correctly positioned. However, radiographic measurement found only 20 cups withing the defined zone. Even if a +2.5° error in radiograph measurements is assumed, only 22 cups were within the defined boundary. Malposition was more common in anteversion (18/50) than in the frontal plane (10/50).

It is therefore accepted that the position of the acetabular cup prosthesis influences wear rates for all types of hip arthroplasty. For metal/polymer articulations, this may be due to the reduced contact area when rim loading occurs. However, problems also occur with other arrangements and large diameter metal on metal bearings may be especially at risk due to increased stress caused by edge loading and possibly also the breakdown of fluid film lubrication. Cup placement is therefore an important aspect of the surgical procedure, especially for the large diameter metal on metal bearings. Surgical technique must emphasise the strongly negative effect of vertically positioned cups, but cups positioned too horizontally may also create problems in terms of impingement and range of motion. It is therefore desirable to provide a system which will reduce the variability in cup position.

Various solutions have been proposed to address the issue of surgical accuracy in cup positioning, the most costly of which is image guided surgery. Although this technique can improve accuracy if used properly, it is extremely expensive and may be beyond the financial resources of many orthopaedic units. There is therefore a need for a simple to use guide which is of low-cost.

A simpler solution was proposed by Echeverri et al in *J. Arthroplasty* 13, Vol 21 No 3, 80-84 2006, "Reliable Acetabular Cup Orientation with a New Gravity-Assisted Guidance System". The proposed arrangement uses two fixed points on the pelvis, the hip joint centre and the anterior superior iliac spine, and two circular "bulls-eye" spirit levels. The first spirit level is fixed to a Schanz pin that is attached to the iliac crest bone, which requires a stab wound over the iliac crest, keeping the pelvis in lateral decubitus, and the second spirit level was attached to the shaft of the introducer/reamer, keeping the shaft in 45° abduction and 15° anteversion. By looking along an attached guide rod and lining it up with the anterior inferior iliac spine, the introducer was kept in the correct location. This arrangement is claimed to give impressive results in experimental testing when compared to the conventional "aerial" style alignment guide. However, the proposed arrangement suffers from various drawbacks in that it requires that the pelvis must be kept vertical throughout the reaming-introducing-impaction processes. In addition, the bulls-eye spirit levels can be difficult to centre.

U.S. Pat. No. 6,743,235 describes a modular instrument for use in positioning an acetabular cup prosthesis. The instrument comprises a hemispherical ball member which is adapted to cooperate with the acetabular prosthetic socket and an alignment shaft which is connected through an orientation pillar to a levelling apparatus. The instrument also has an intermediate shank, a distal handle and an impaction knob. The lower end of the orientation is coupled and anchored into the shank of the alignment shaft at an oblique angle of 135°. The upper end of the orientation pillar is provided with a levelling apparatus and the intermediate part of the orientation pillar is provided with a laser pen apparatus. When the acetabular cup is correctly positioned, the alignment shaft is abducted at an abduction angle of 45° such that the orientation pillar becomes perpendicular to the floor of the operating room or to the horizontal axis of the patient and the air bubble in the levelling apparatus migrates to the centre. The laser pen apparatus is located in a tray connected to the alignment shaft by a hinge mechanism. However, it is an independent parameter, adjustable as to the anteversion for the acetabular cup prosthesis. Once in position, the laser pen apparatus is switched on such that the beam projects across the acetabulum or pelvis while fine adjustments in the angel of anteversion are made.

In U.S. Pat. No. 6,743,235 it is suggested that the device should be angled at 45° to the vertical with respect to the earth, not to the pelvis as it is stated that if the pelvis is not in strict lateral decubitus, the cup will not be inserted at 45° to the pelvis. As the whole pelvis apart from the acetabulum is obscured by drapes, soft tissues or blood during surgery, keeping it in strict lateral decubitus during surgery is difficult.

In *J. Arthroplasty* 19:992-997, 2004, "lIntraoperative Pelvic Motion on Total Hip Arthroplasty", Asayama et al report that the pelvis can move up to 9° in the frontal plane, 31° in the horizontal plane and 18° in the sagittal plane during surgery. Such movement introduces serious inaccuracies into the cup angle position.

An alternative arrangement is described in U.S. Pat. No. 6,214,014. Here an apparatus is used to estimate the actual inclination of the acetabulum. A compensation is then made using a goniometer. A laser pointer is inserted into the end of the goniometer and a target can be marked on the wall of the operating theatre. The surgeon then uses this target to align the insertion tool for the acetabular prosthesis. The position can be rechecked after insertion by re-aiming at the target Whilst the laser pointing device may be inserted into an aperture at the end of the insertion tool to check the position, the laser pointing device is not present during the impaction.

There is therefore still a need for a system which is simple to use and which will provide a reliable means to enable a surgeon to ensure that the acetabular cup prosthesis is correctly aligned. It is also desirable to provide an apparatus that is of low cost.

SUMMARY OF THE INVENTION

According to a first aspect of the present invention there is provided a trial acetabular cup having a signal generating device located thereon.

An insertion tool may then be provided having a signal generating device located such as to project a signal outwardly in a direction substantially outwardly through the pole in the base of the bowl of the acetabular cup. By activating the signal generating device and then aligning the resultant signal with the mark made relating to the signal from the trial acetabular cup, the surgeon can implant the acetabular cup prosthesis accurately via the position established as the optimum insertion position using the trial acetabular hip prosthesis. Although it is desirable that the surgeon is able to align the signal accurately with the mark, small deviations will still mean that the cup prosthesis is implanted within acceptable tolerances.

According to a third aspect of the present invention there is provided a post capable of being inserted into the bone of the pelvis and having a signal generating device located thereon.

According to a fourth aspect of the present invention there is provided an apparatus system for use in the implantation of an acetabular cup prosthesis comprising a trial acetabular cup of the above first aspect and an insertion tool. The insertion tool may be a conventional insertion tool or may be that of the above second aspect of the present invention. The system optionally includes the post of the above third aspect.

According to a fifth aspect of the present invention there is provided a kit comprising at least one trial acetabular cup of the above first aspect and at least insertion tool. The insertion tool may be a conventional insertion tool or may be that of the above second aspect. The kit preferably also includes at least one acetabular cup prosthesis. The kit further optionally includes the post of the above third aspect.

According to a sixth aspect of the present invention there is provided a method for inserting an acetabular cup prosthesis comprising the steps of:
  inserting the trial acetabular cup of the above first aspect into the acetabulum;
  activating the signal generating device of the above first aspect to produce at least one first signal;
  placing a mark where the first signal impacts on a surface;
  removing the trial acetabular cup of the above first aspect;
  positioning an acetabular cup prosthesis with an insertion tool in the acetabulum in the acetabulum;
  activating the signal generating device to produce a second signal;
  aligning the second signal with the mark; and
  inserting the acetabular cup prosthesis.

According to a seventh aspect of the present invention there is provided a method for inserting an acetabular cup prosthesis comprising the steps of:
  inserting the post of the above third aspect into the pelvis;
  inserting the trial acetabular cup of the above first aspect into the acetabulum;
  activating the signal generating device of the above first aspect to produce an at least one first signal;
  adjusting the signal generating device with respect to the post so that the at least one third signal produced therefrom coincides with the point at which the at least one first signal impinges on a surface;
  removing the trial acetabular cup of the above first aspect;
  positioning an acetabular cup prosthesis with an insertion tool in the acetabulum;
  activating the signal generating device of the insertion tool to produce an at least one second signal;
  aligning the at least one second signal with the at least one third signal; and
  inserting the acetabular cup prosthesis.

Thus according to the eighth aspect of the present invention, there is provided a target mounted on an arm insertable into the patient, said target comprising a tube. The target may additionally include a plate located on the tube. The plate may be a disc.

According to a ninth aspect of the present invention there is provided an apparatus system for use in the implantation of an acetabular cup prosthesis comprising a trial acetabular cup of the above first aspect and a target of the above eighth aspect.

According to a tenth aspect of the present invention there is provided a kit comprising at least one trial acetabular cup of the above first aspect and at least one target of the above eighth aspect.

According to an eleventh aspect of the present invention there is provided a method for inserting an acetabular cup prosthesis comprising the steps of:
  connecting the target of the above eighth aspect to the patient;
  inserting the trial acetabular cup of the above first aspect into the acetabulum;
  activating the signal generating device of the trial acetabular cup of the first aspect to produce a signal;
  adjusting the position of the target such that the signal passes through the target;
  removing the trial acetabular cup of the above first aspect;
  positioning an acetabular cup prosthesis with an insertion tool in the acetabulum in the acetabulum;
  activating the signal generating device to produce a second signal;
  aligning the second signal with the target; and
  inserting the acetabular cup prosthesis.

According to a twelfth aspect of the present invention there is provided a method for inserting an acetabular cup prosthesis comprising the steps of:
  inserting the trial acetabular cup of the above first aspect into the acetabulum;
  inserting a guide pin into the pelvis;
  locating a target on the guide pin;
  removing the trial acetabular cup of the above first aspect;
  positioning an acetabular cup prosthesis with an insertion tool in the acetabulum in the acetabulum;
  activating the signal generating device on the insertion tool to produce a signal;
  aligning the signal with the target; and
  inserting the acetabular cup prosthesis.

BRIEF DESCRIPTION OF THE DRAWINGS

The invention will now be described by way of example with reference to the accompanying drawings in which.

Corresponding reference characters indicate corresponding parts throughout the drawings.

DETAILED DESCRIPTION OF THE DRAWINGS

Figure 1:
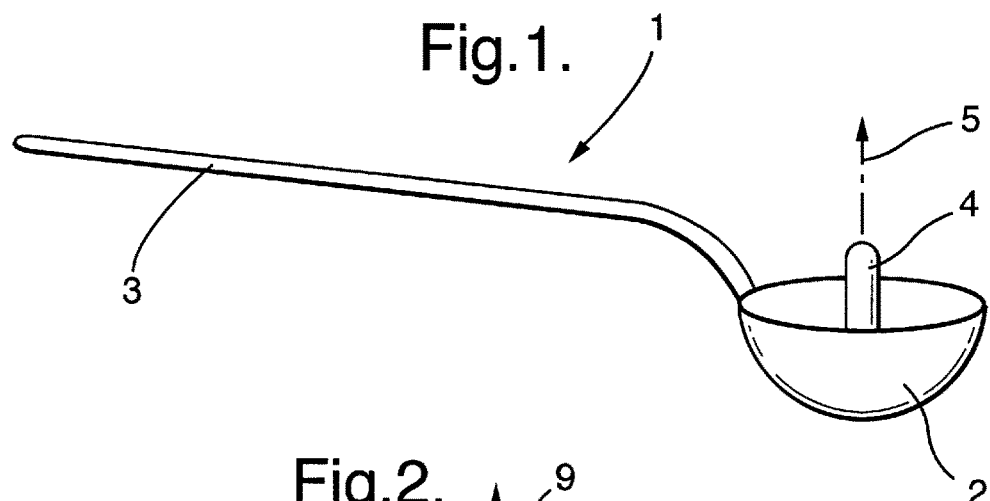
FIG. 1 is a perspective view of one arrangement of the first aspect of the present invention.
Figure 2:
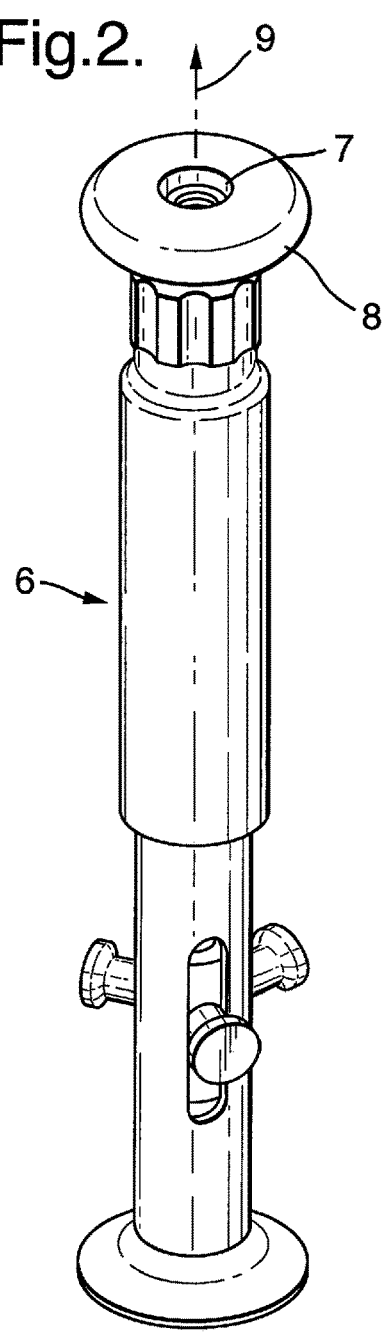
FIG. 2 is a perspective view of one example of an insertion tool.
Figure 3:
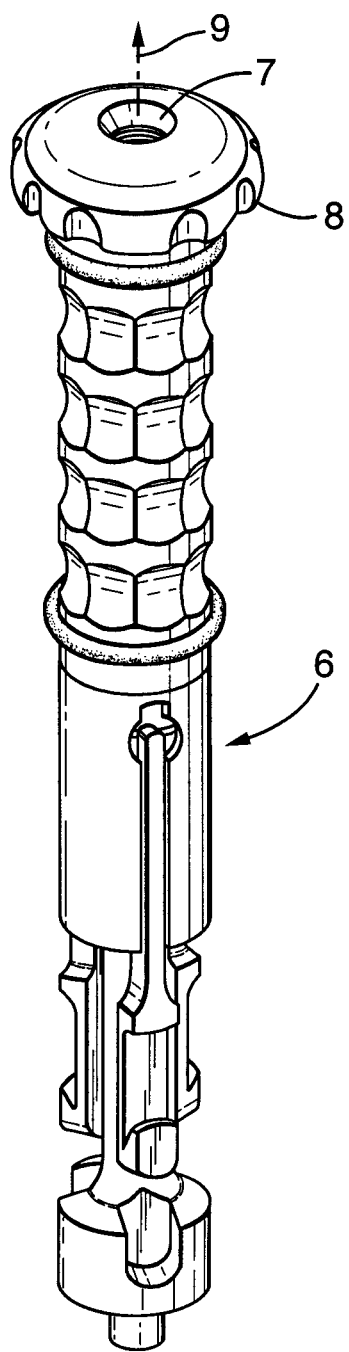
FIG. 3 is a perspective view of a second example of an insertion tool.
Figure 4:
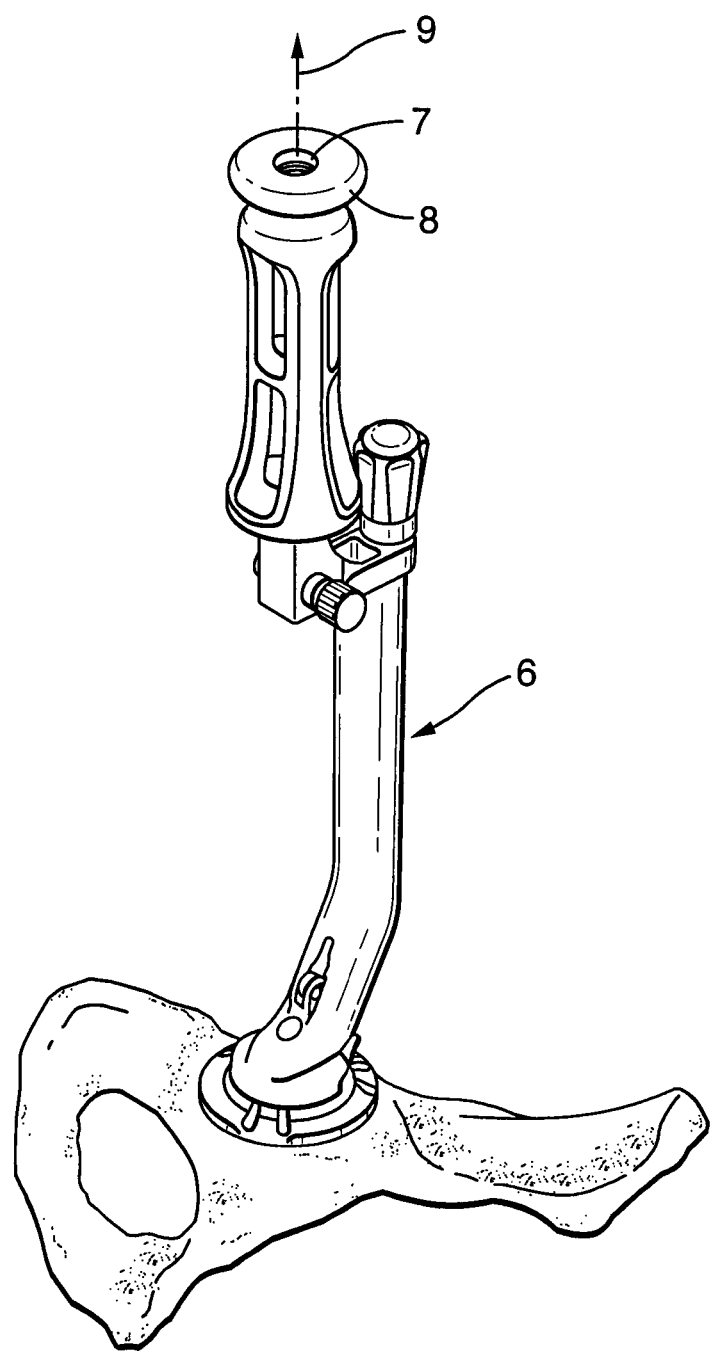
FIG. 4 is a perspective view of a third example of an insertion tool.
Figure 5:
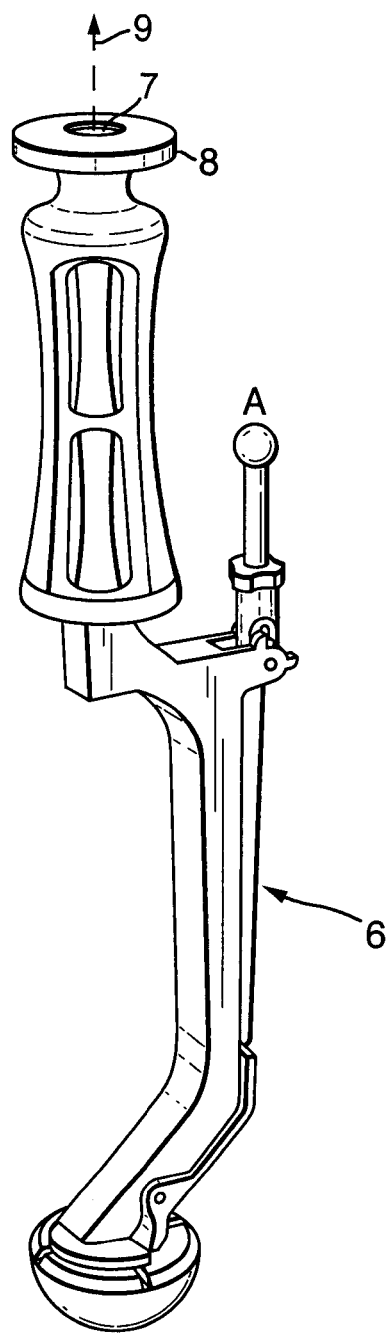
FIG. 5 is a perspective view of a fourth example of an insertion tool.

For ease of reference the invention will be described with reference to a laser generating device. However, it will be understood that any signal generating device can be used.

In a first aspect, the present invention, relates to a trial acetabular cup 1. In the illustrated embodiment the trial cup 1 comprises a bowl 2 and a handle 3. A laser generating device 4, such as a laser pen, is located in the bowl such that when it is operated, a beam 5 is directed outwardly along the axis passing through the pole of the bowl.

Once the surgeon has the trial acetabular cup in the correct position, the laser can be activated and the point at which the beam impinges the operating theatre wall or ceiling is marked. The acetabular cup is then applied using an impaction tool. Examples of these tools 6 are illustrated in FIGS. 2 to 5. Each of these impaction tools 6 an impaction knob 8 having a bore 7 therein. The laser generating device is located in the bore such that the beam 9 projects outwardly therefrom and along the central axis thereof. When the surgeon has aligned the point at which the beam 9 impacts the operating theatre with the mark made of the point at which the beam from the trial acetabular cup impinged the theatre, the acetabular cup prosthesis will be in the correct position and can be inserted.

Figure 6:
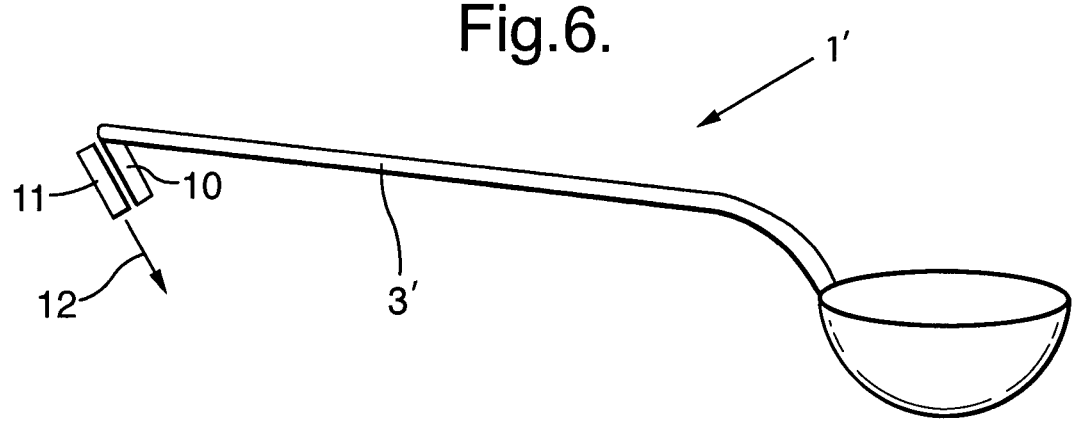
FIG. 6 is a perspective view of an alternative trial acetabular cup.

An alternative trial acetabular cup 1' is illustrated in FIG. 6. Here the handle 3' includes a platform 10 on which the laser generating device is located. In the illustrated embodiment the beam 12 is illustrated as extending downwardly from the trial acetabular cup 1'. However, it will be understood that the device can be located such that the beam extends in any direction.

Figure 7:
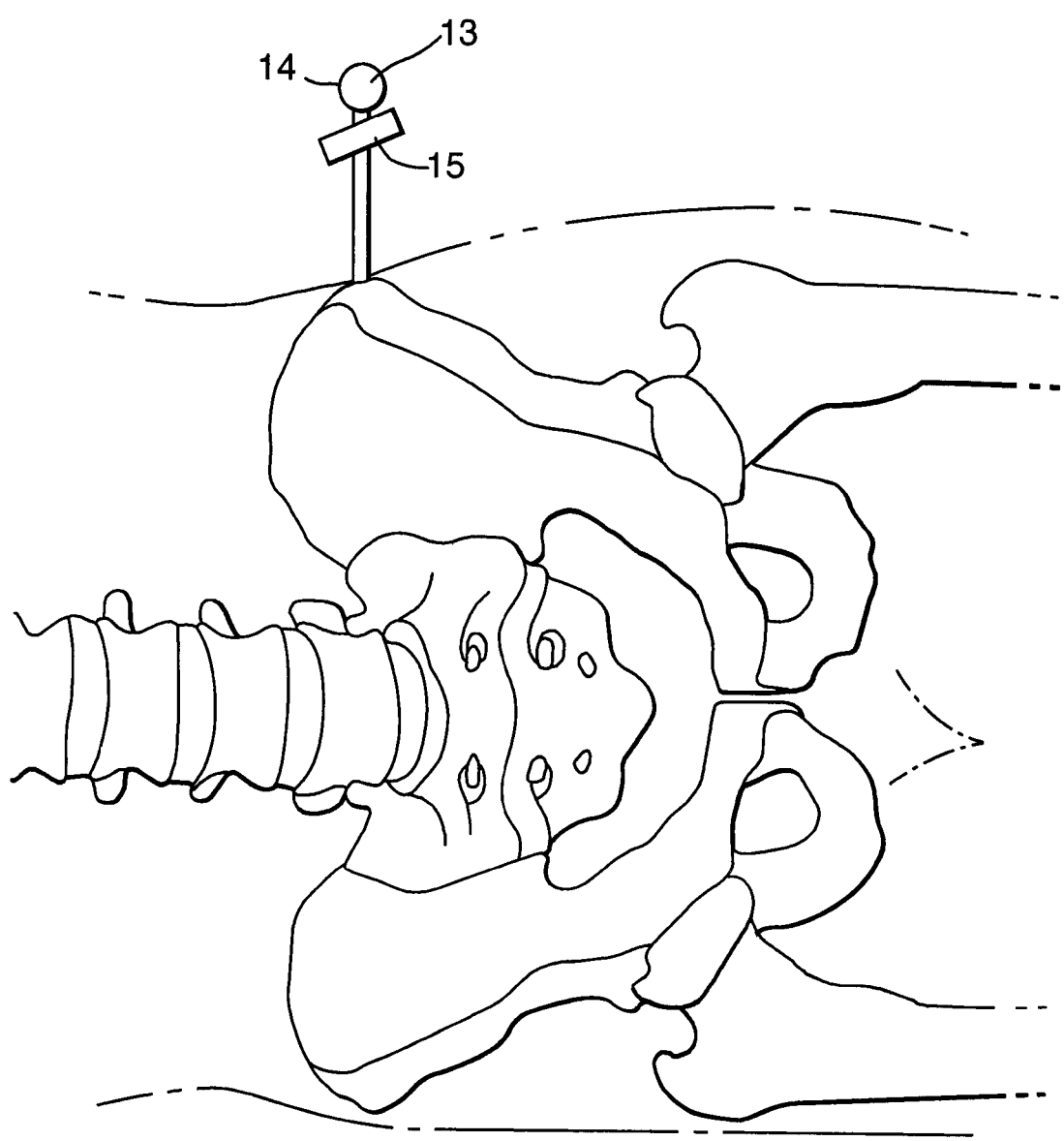
FIG. 7 is a schematic view of the post of the third aspect of the present invention in position in the pelvis.

FIG. 7 illustrates the third component, i.e. the post, which in use is inserted into the pelvis. The post may be inserted into any position in the pelvis. A knob 14 may be located onto the end of the post such that there is no sharp end of the post A laser generating device 15 is located on the shaft on the post and is movable thereto both around the post and with an angle thereto.

Figure 8:
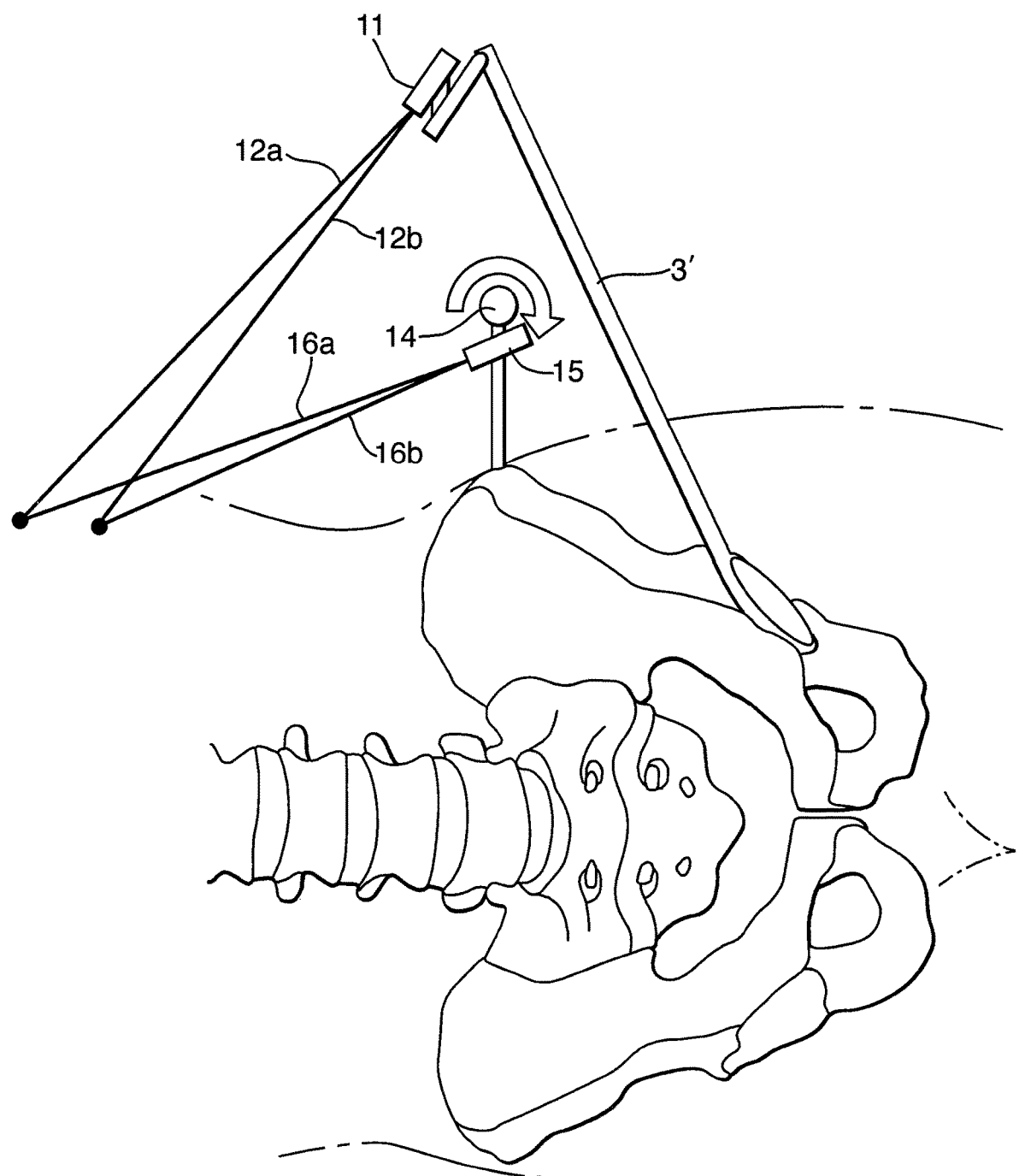
FIG. 8 is a schematic view of the laser beams from the trial acetabular cup prosthesis of FIG. 6 and from the post of the third aspect of the present invention.
Figure 9:
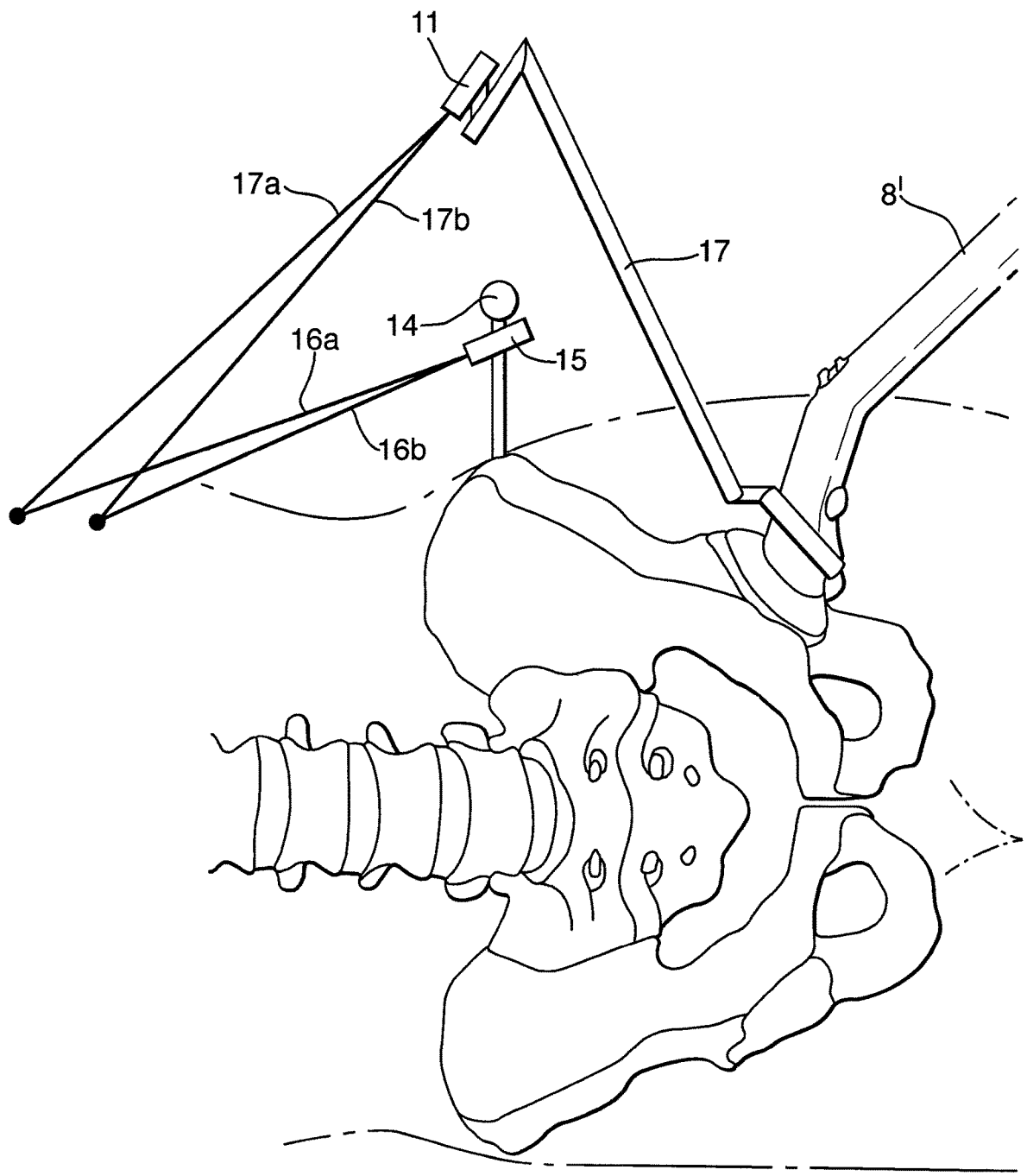
FIG. 9 is a schematic view of one example of the laser beams from the insertion tool of the second aspect of the present invention and from the post of the third aspect of the present invention.
Figure 10:
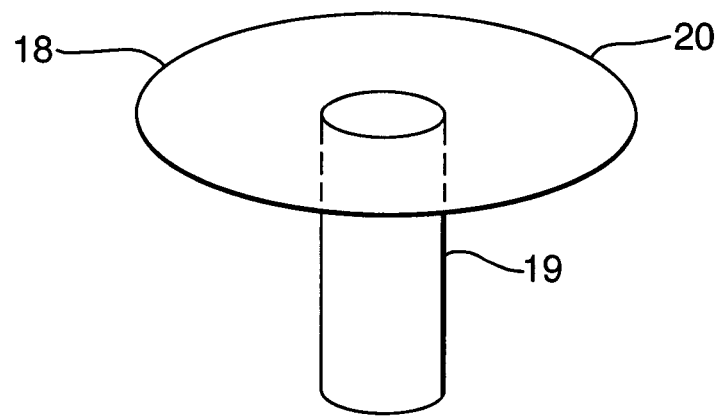
FIG. 10 is a schematic view of a target of the eighth aspect of the present invention.

In use the trial acetabular cup 1' is positioned in the acetabulum and when the surgeon is happy with its position, the laser generating device 4 is activated to produce two beams 12a, 12b which will impinge on a surface in the operating theatre. The laser generating device 15 located on the post 14 is activated and two beams 16a, 16b are produced. The laser generating device 15 is then moved with respect to the post 14 until the two beams 16a and 16b impinge on the same point of the operating theatre as the beams 12a and 12b from the laser operating device on the platform of the trial acetabular cup. This is illustrated in FIG. 8.

The trial acetabular cup 1' can then be removed and the acetabular cup located in the pelvis using the tool 8'. A temporary arm 17 is connected to the tool 8'. The arm 17 is configured so that it is at the same position in space as the handle 3' of the trial acetabular cup 1'. The laser generating device 11 is then activated and the tool and hence the arm are then adjusted until beams 17a and 17b impinge on the same point of the operating theatre as the beams 16a and 16b from the laser generating device on the post 14. The surgeon will then know that the acetabular cup is located in the correct position and he can then commence the insertion.

Figure 11:
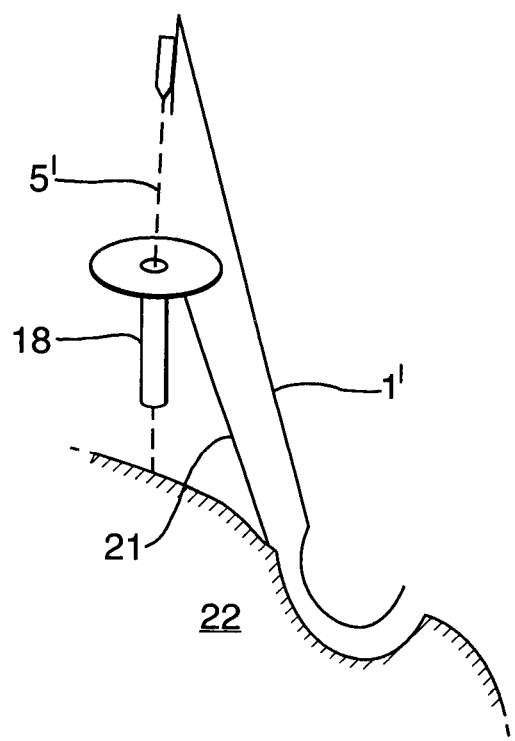
FIG. 11 is a schematic illustration of the trial acetabular cup of the present invention being used in combination with the target of FIG. 10.

In an alternative arrangement of the present invention, a target 18 is used. The target 18 comprises a hollow tube 19 having a disc 20 mounted thereon. As illustrated in FIG. 11, the target 18 is located on a positionable arm 21 to the pelvis 22. Once the surgeon has the trial acetabular cup 1' is in the correct position, the target 18 is adjusted on the arm 21 such that the beam 5' from the laser generating device 4' passes through the tube 19 of the target 18.

Figure 12:
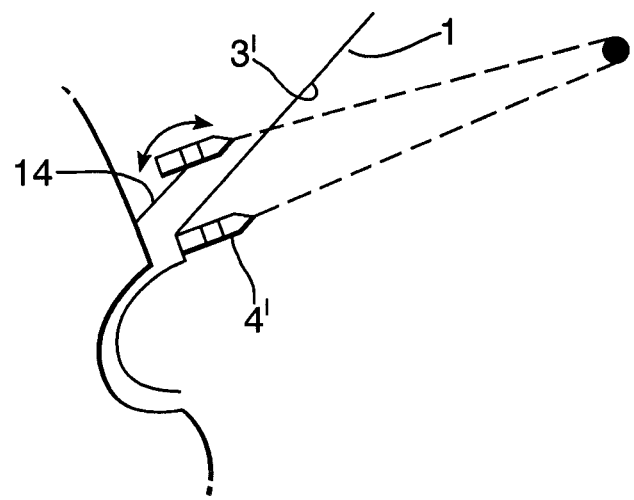
FIG. 12 is a schematic illustration of an alternative trial acetabular cup of the present invention being used in combination with the post of the present invention.
Figure 13:
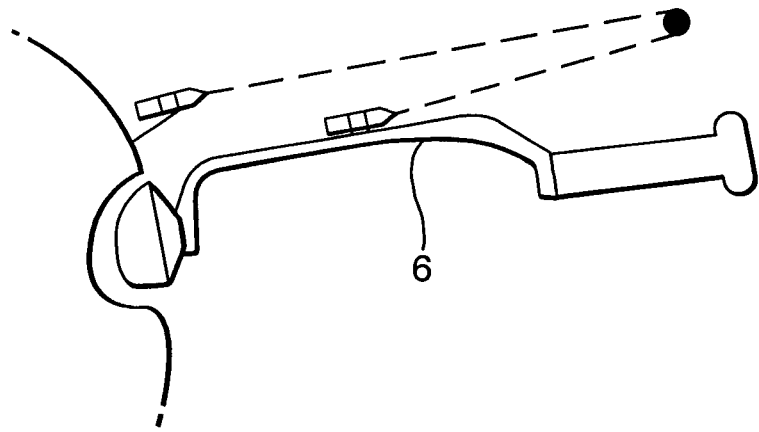
FIG. 13 is a schematic illustration of the insertion tool following the arrangement of FIG. 12.

In FIG. 12 an arrangement in which the laser generating device 4' is locating on the trial acetabular cup 1 such that it is located on the handle 3' at a position adjacent to the bowl. A post 14 is located in the pelvis. Once the trial acetabular cup is in the correct position, the laser generating on the handle is activated and the laser generating device on the post 14 is adjusted such that the beams impinge on the same position. The trial acetabular cup is then removed and the insertion tool 6 is used. Once the laser generating device on the insertion tool is activated, the surgeon needs to align the beam with that from the laser generating device on the post. Once the beams are aligned, the prosthesis can be inserted. This is illustrated in FIG. 13.

Figure 14:
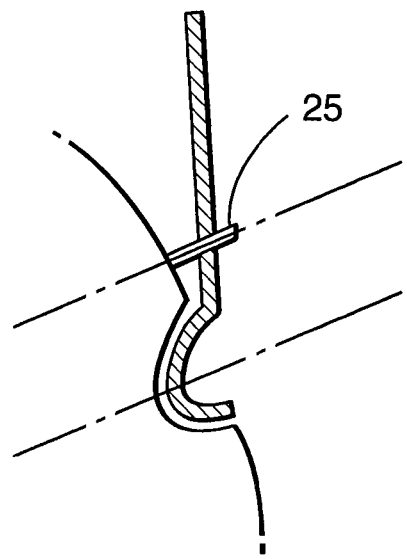
FIG. 14 is a schematic illustration of the insertion of the guide pin.
Figure 15:
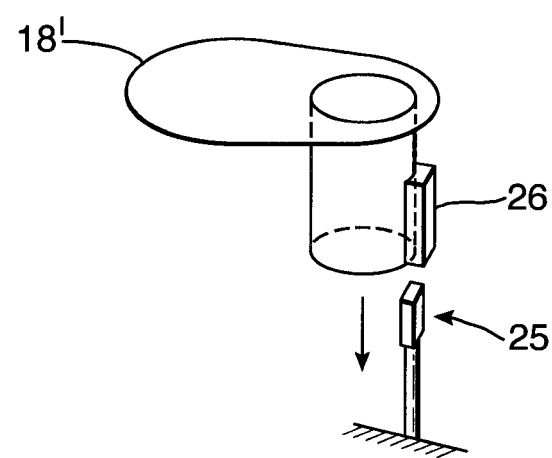
FIG. 15 is a schematic illustration of the use of a target on the guide pin.

An alternative arrangement is illustrated in FIG. 14. In this arrangement, once the trial acetabular cup prostheses is in the correct position, a guide pin 25 is inserted into the pelvis through an aperture in the handle of the trial acetabular cup. Once the trial acetabular cup is removed, a target 18' is connected to the guide pin 25. A connector 26 is provided on the tube 19 to connect to the guide pin. A portion of the guide pin and the connector may be shaped to interconnect such that the target cannot move once it has been located in position. This is illustrated in FIG. 15.

Figure 16:
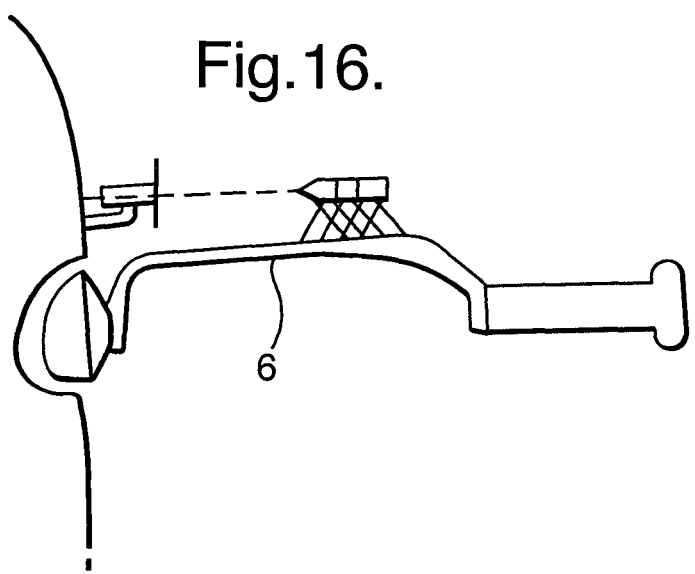
FIG. 16 is a schematic illustration of an insertion tool having a signal generating device being used in combination with the target of FIG. 15.

The insertion tool 6 is then used. Once the laser generating device on the insertion tool is activated, the surgeon needs to align the beam such that it passes through the tube in the target 18'. Once the beam is in the correct position, the prosthesis can be inserted. This is illustrated in FIG. 16.

DETAILED DESCRIPTION OF THE INVENTION

According to a first aspect of the present invention there is provided a trial acetabular cup having a signal generating device located thereon.

Trial acetabular cups, also known as phantom prostheses, are well known in the art and any suitable arrangement may be used. Whatever the configuration of the trial acetabular cup, they will all include a bowl which is of a configuration corresponding to that of an acetabular cup prosthesis. For the apparatus of the present invention, these known trial cups are modified to include the signal generating device arranged such that the signal is directed as desired.

In one arrangement, the signal generating device may be located in the bowl of the cup. The signal generating device may be positioned such that when it is activated, the signal is directed along an axis passing outwardly through the pole in the base of the bowl. In a modification of this arrangement, the signal generating device may be located such that the line along which the signal travels is not precisely aligned with the axis passing through the pole in the base of the bowl. Although this arrangement will introduce a margin of error of a few degrees when used as described below, even with this margin of error, the acetabular cup prosthesis will still be inserted with greater accuracy than has been achievable heretofore with prior art devices.

In use, the trial acetabular cup will be used in conventional manner, once the surgeon is satisfied that the trial acetabular cup is in the correct position, the signal generating device can be activated. The position of impaction of the signal with a surface is then marked. The position will depend on the positioning of the patient but will generally be a wall or the ceiling of the operating theatre. In one arrangement, a screen may be used and the signal will impact on the screen. A mark can then be made where the signal impacts the surface. The mark may be made by any suitable means. The mark can be a physical mark or, for example, where the signal is not a visible signal, marking may be noted by any suitable means and may be an electronic marking.

An insertion tool may then be provided having a signal generating device located such as to project a signal outwardly in a direction substantially outwardly through the pole in the base of the bowl of the acetabular cup. By activating the signal generating device and then aligning the resultant signal with the mark made relating to the signal from the trial acetabular cup, the surgeon can implant the acetabular cup prosthesis accurately via the position established as the optimum insertion position using the trial acetabular hip prosthesis. Although it is desirable that the surgeon is able to align the signal accurately with the mark, small deviations will still mean that the cup prosthesis is implanted within acceptable tolerances.

For ease of handling, the trial acetabular cup may have a handle extending from a point on the rim of the cup. The handle may be fixed or detachable. It may be of any suitable configuration but in one arrangement, it may extend initially upwardly and then radially from the rim such that the arrangement resembles a spoon. These spoon-like acetabular trial prothesis are known in the art. In use, the handle is held during the trial reduction of the femur and the patients leg is manipulated throughout the desirable range of motion. Whilst manipulating the patients leg, the surgeon also manipulates the trial acetabular cup with the handle such that a position is found where there is no impingement of the femur on the cup throughout the desirable range of motion. This position of the cup is then defined as the correct position. Once the correct position is established, the signal generating device can be activated.

As in the above mentioned arrangement, the signal generating device may be located in the bowl. Alternatively, the signal generating device may be located on the handle. The signal generating device may be located at any suitable position on the handle. In one arrangement the signal generating device is located on the handle at a point adjacent to, or substantially close to, the bowl of the trial acetabular cup and is positioned to direct the signal outwardly from the patient.

In one alternative arrangement the signal generating device may be located at the end of the handle remote from the bowl of the trial acetabular cup. Where the signal generating device on the handle is located adjacent to the bowl, the signal generating device on the insertion tool will be located on an appropriate position to be as close as possible to that of the signal generating device on the handle of the trial acetabular cup.

The signal generating device may be located such that the signal points in any selected direction however, it will generally be fixed with respect to the handle. In one arrangement, the handle has a platform extending at an angle thereto and located at the end thereof remote from the bowl of the trial acetabular cup; the signal generating device will then be located on the platform.

Thus, according to a second aspect of the present invention, there is provided an insertion tool for inserting an acetabular cup prosthesis, said insertion tool comprises: an arm extending outwardly therefrom which in use will have a corresponding configuration to a handle of a trial acetabular cup; and having a signal generating apparatus located thereon at a corresponding position to that of the handle on the trial acetabular cup.

The arm may be a fixed component of the insertion tool or may be detachable therefrom. Where the arm is detachable, the arm may be connected to the insertion tool by any suitable means. In one arrangement, prongs may be provided on the end of the arm which can be inserted into corresponding slots on the insertion tool.

The insertion tool of this embodiment or of that described above may be of any suitable configuration. The tool will generally be selected to correspond to, and interact with, the acetabular cup prosthesis selected for insertion into the patient and/or any cap for the prosthesis used as part of the insertion process. Examples of suitable insertion tools can be found in GB2323036, EP1634552 and EP 1721586 which are incorporated herein by reference. In the arrangement of the second embodiment of the present invention, these insertion tools will be modified to include the handle.

Whilst the apparatus of the present invention offers substantial advantages over the prior art, difficulties may occur if the orientation of the patient is altered between the mark being made using the trial acetabular cup of the present invention and the cup being introduced. It is therefore desirable to provide an arrangement which further enhances the accuracy of the insertion of the prosthesis enhanced by the use of a second signal generating arrangement.

According to a third aspect of the present invention there is provided a post capable of being inserted into the bone of the pelvis and having a signal generating device located thereon.

The post may be made of any suitable material. The material will be selected to be compatible with its introduction into the body both from a safety perspective but also to ensure that it has sufficient strength for insertion into the pelvis.

The signal generating device is preferably movable with respect to the post. It may be movable such that its position about the axis of the post may be adjusted, it may be movable such that its angle to the post may be adjusted or it may be movable such that both its position about the post and its angle to the post may be adjusted. The signal generating device may be connected to the post by any suitable means provided that the required level of movability is available. In a preferred arrangement, means will be provided to lock the laser generating device in position. Suitable devices include clamps, screws, bolts and the like.

In this arrangement, where the three components are to be used, in use the surgeon will locate the post at any position on the pelvis. The post will need to be fixed in position until the insertion of the acetabular cup prosthesis is completed and thus the post is implantable in the bone. The surgeon then places the trial acetabular cup into the desired position in the pelvis. Once the surgeon has manipulated the patient and the trial acetabular cup in conventional manner to locate the correct position, the signal generating device will be activated such that the signal travels outwardly and will impact on a surface in the operating theatre. The position will depend on the positioning of the patient but will generally be a wall or the ceiling. In one arrangement, a screen may be used and the signal will impact on the screen. In this arrangement, there is no requirement to make a mark. Instead, the surgeon will activate the signal generating device on the post and then adjust its position such that the signal impinges on the point of impact of the signal from the trial cup.

The trial cup is then removed and the alignment cup prosthesis is inserted using an insertion tool which may be either conventional or may be of the above second aspect. As the cup on the insertion tool is positioned ready for insertion, the signal generating device on the tool is activated. The surgeon need then simply align the signal from the tool with the point of impact of the signal from the signal generating device on the post. Once the signals are aligned, the surgeon can implant the cup prosthesis with the knowledge that the cup is correctly aligned.

Although it is desirable that the surgeon is able to align the signals accurately with the mark, small deviations will still mean that the cup prosthesis is implanted within acceptable tolerances.

To further improve accuracy, the signal generating device in the trial acetabular cup, insertion tool and, where present, the post of the above third component, may produce two or more signals extending at different angles or may comprise two or more signals generating devices each generating a signal. In this arrangement, the positioning of the devices will be selected such that for each component, the signals project at corresponding angles such that in use the surgeon will make more than one mark and then align the other signals accordingly.

According to a fourth aspect of the present invention there is provided an apparatus system for use in the implantation of an acetabular cup prosthesis comprising a trial acetabular cup of the above first aspect and an insertion tool. The insertion tool may be a conventional insertion tool or may be that of the above second aspect of the present invention. The system optionally includes the post of the above third aspect.

According to a fifth aspect of the present invention there is provided a kit comprising at least one trial acetabular cup of the above first aspect and at least insertion tool. The insertion tool may be a conventional insertion tool or may be that of the above second aspect. The kit preferably also includes at least one acetabular cup prosthesis. The kit further optionally includes the post of the above third aspect.

According to a sixth aspect of the present invention there is provided a method for inserting an acetabular cup prosthesis comprising the steps of:
  inserting the trial acetabular cup of the above first aspect into the acetabulum;
  activating the signal generating device of the above first aspect to produce at least one first signal;
  placing a mark where the first signal impacts on a surface;
  removing the trial acetabular cup of the above first aspect;
  positioning an acetabular cup prosthesis with an insertion tool in the acetabulum in the acetabulum;
  activating the signal generating device to produce a second signal;
  aligning the second signal with the mark; and
  inserting the acetabular cup prosthesis.

The insertion tool may be a conventional insertion tool or the insertion tool of the above second aspect.

According to a seventh aspect of the present invention there is provided a method for inserting an acetabular cup prosthesis comprising the steps of:
  inserting the post of the above third aspect into the pelvis;
  inserting the trial acetabular cup of the above first aspect into the acetabulum;
  activating the signal generating device of the above first aspect to produce an at least one first signal;
  adjusting the signal generating device with respect to the post so that the at least one third signal produced therefrom coincides with the point at which the at least one first signal impinges on a surface;
  removing the trial acetabular cup of the above first aspect;
  positioning an acetabular cup prosthesis with an insertion tool in the acetabulum;
  activating the signal generating device of the insertion tool to produce an at least one second signal;
  aligning the at least one second signal with the at least one third signal; and
  inserting the acetabular cup prosthesis.

The insertion tool may be a conventional insertion tool or the insertion tool of the above second aspect.

In an alternative arrangement of the first aspect of the present invention, a platform is located at the end of a handle of the trial acetabular cup and the signal generating device is located on the platform such that the signal is directed downwardly towards the patient.

A positionable arm having a target located thereon is attached to the patient. Generally, the positionable arm is attached to the pelvis of the patient. The arm is preferably rigidly attached to the patient.

The target may be of any suitable configuration. In one arrangement, the target comprises a tube. The tube may be of any cross section. It may have a circular configuration. The target may be the tube alone or may additionally include a plate, which may be in the form of the disc, to assist the user to locate the tube.

use, the trial acetabular cup of the present invention with the signal generating device located on the platform and directed downwardly towards the patient is used in conventional manner. Once the surgeon has the trial acetabular cup in the optimum position using conventional techniques, the signal generating device is activated and the target adjusted such that the signal passes through the target. Where the target is a tube, the target is preferably adjusted such that the signal passes through the target without touching the sides of the tube.

In use, an introducer tool will be used with a handle having a signal introducing device in a position corresponding to that on the trial acetabular cup. As the introducer tool is used, the tool is aligned such that the signal passes through the target, preferably without touching the sides. Once this is achieved the cup can be impacted.

Thus according to the eighth aspect of the present invention, there is provided a target mounted on an arm insertable into the patient, said target comprising a tube. The target may additionally include a plate located on the tube. The plate may be a disc.

According to a ninth aspect of the present invention there is provided an apparatus system for use in the implantation of an acetabular cup prosthesis comprising a trial acetabular cup of the above first aspect and a target of the above eighth aspect.

According to a tenth aspect of the present invention there is provided a kit comprising at least one trial acetabular cup of the above first aspect and at least one target of the above eighth aspect.

According to an eleventh aspect of the present invention there is provided a method for inserting an acetabular cup prosthesis comprising the steps of:
 connecting the target of the above eighth aspect to the patient;
 inserting the trial acetabular cup of the above first aspect into the acetabulum;
 activating the signal generating device of the trial acetabular cup of the first aspect to produce a signal;
 adjusting the position of the target such that the signal passes through the target;
 removing the trial acetabular cup of the above first aspect;
 positioning an acetabular cup prosthesis with an insertion tool in the acetabulum in the acetabulum;
 activating the signal generating device to produce a second signal;
 aligning the second signal with the target; and
 inserting the acetabular cup prosthesis.

In an alternative arrangement, the trial acetabular cup does not have a signal generating device. When the optimum position is located a guide pin can be inserted into the pelvis. In this arrangement, the trial acetabular cup may include a guide-hole in the handle through which the pelvis can be drilled and/or the guide pin inserted. Once the guide pin has been inserted, a target of the above eighth aspect of the present invention may be connected to the guide pin. The target may be connected in the guide pin by any suitable means. In one arrangement, a connector may be connected to the tube of the target. The head of the guide pin may be shaped to engage with the connector of the tube in any suitable manner and preferably prevent the rotation thereof.

Once the target is in place, an introducer tool connected to an acetabular cup prosthesis and having a signal generating device connected thereto such that the signal is directed downwardly. The introducer tool in this arrangement will have the signal generating device attached near the centre-line. The introducer tool is then adjusted such that the signal generating device passes through the target. Once in the correct position, the acetabular cup prosthesis can be impacted.

According to a twelfth aspect of the present invention there is provided a method for inserting an acetabular cup prosthesis comprising the steps of:
 inserting the trial acetabular cup of the above first aspect into the acetabulum;
 inserting a guide pin into the pelvis;
 locating a target on the guide pin;
 removing the trial acetabular cup of the above first aspect;
 positioning an acetabular cup prosthesis with an insertion tool in the acetabulum in the acetabulum;
 activating the signal generating device on the insertion tool to produce a signal;
 aligning the signal with the target; and
 inserting the acetabular cup prosthesis.

Any suitable signal generating device may be used. In one arrangement a laser generating device may be used. However, other means of generating a signal whether visible or otherwise may be used. One benefit of a visible signal such as that generated by a laser or other light source is that it is generally of low cost to manufacture and is easily used. As the point at which a light beam from a laser or other light emitting device impacts on a surface will be easily seen, the location of the point of impaction can be readily marked by a user. However means for generating signals of other types such as acoustic, infra-red and the like may be used. With these arrangements, specialised receivers may be required to indicate the point of impaction of the signal with a surface.

Where a laser generating device is used, any suitable laser generating device may be used. In one arrangement, the laser generating device will be of the kind used in laser pointer devices. These devices utilize semiconductor lasers that are powered from an internal battery and have dimensions similar to that of an ordinary pen. Such devices are well known in the art and are therefore not detailed here.

The trial acetabular cup of the present invention may include markers such that they can be used with surgical navigation systems. Such systems are well known in the art and are therefore not detailed here. In one arrangement the markers are reflective markers which can be tracked using, for example, infrared techniques. Similar tracking systems may be provided with the insertion tool and or the post of the present invention.

When introducing elements of the present invention or the preferred embodiment(s) thereof, the articles "a", "an", "the" and "said" are intended to mean that there are one or more of the elements. The terms "comprising", "induding" and "having" are intended to be inclusive and mean that there my be additional elements other than the listed elements.

In view of the above, it will be seen that the several objects of the invention are achieved and other advantageous results attained.

As various changes could be made in the above constructions, products and methods without departing from the spirit and scope of the invention it is intended that all matter contained in the above description and shown in the accompanying drawings shall be interpreted as illustrative and not in a limiting sense.

What is claimed is:

1. A kit for use in the implantation of an acetabular cup prosthesis comprising a trial acetabular cup for positioning in a patient's acetabulum, the trial acetabular cup having a light source mounted directly thereon, the light source being configured for generating and emitting a light signal away from the trial acetabular cup when the trial acetabular cup is in the acetabulum, and an insertion tool having a light source mounted thereon, the insertion tool being configured for inserting the acetabular cup prosthesis into the patient's acetabulum, wherein the insertion tool comprises an arm extending outwardly therefrom and the trial acetabular cup comprises a handle, the arm of the insertion tool having a corresponding configuration to the handle of a trial acetabular cup and having a light source located thereon.

2. A kit according to claim 1 wherein the kit includes a post capable of being inserted into the bone of the pelvis and having a light source located thereon.

3. A kit according to claim 1 wherein the kit also includes the acetabular cup prosthesis having a light source mounted thereon configured for emitting light away from the acetabular cup prosthesis.

4. A kit according to claim 1 wherein the cup comprises a bowl and the light source is mounted directly in the bowl.

* * * * *